US011097001B1

(12) United States Patent
Deisseroth (10) Patent No.: US 11,097,001 B1
(45) Date of Patent: Aug. 24, 2021

(54) COMPOSITION AND METHOD AGAINST TUBERCULOSIS (71) Applicant: MicroVAX, LLC, Warrenton, VA (US)

(72) Inventor: Albert B. Deisseroth, Potomac, MD (US)

(73) Assignee: MicroVAX, LLC, Warrenton, VA (US)

( * ) Notice: Subject to any disclaimer, the term of this patent is extended or adjusted under 35 U.S.C. 154(b) by 208 days.

(21) Appl. No.: 15/421,689

(22) Filed: Feb. 1, 2017

Related U.S. Application Data (60) Provisional application No. 62/290,058, filed on Feb. 2, 2016.

(51) Int. Cl.
A61K 39/04 (2006.01)
C12N 15/86 (2006.01)
C12N 7/00 (2006.01)
A61K 39/00 (2006.01)

(52) U.S. Cl.
CPC ............... A61K 39/04 (2013.01); C12N 7/00 (2013.01); C12N 15/86 (2013.01); A61K 2039/5256 (2013.01); C12N 2710/10343 (2013.01)

(58) Field of Classification Search
None
See application file for complete search history.

(56) References Cited

PUBLICATIONS

Bowie et al (Science, 1990, 257:1306-1310).*
Greenspan et al. (Nature Biotechnology 7: 936-937, 1999).*
Yasir A. W. Skeiky et al., Advances in tuberculosis vaccine strategies, Nature Reviews Microbiology, vol. 4, p. 469-476, Jun. 2006.
Lorenza Favrot et al., Targeting the mycobacterial envelope for tuberculosis drug development, Expert Rev Anti Infect Ther., vol. 10, No. 9, p. 1-26, Sep. 2012.
Harald G. Wiker et al., The Antigen 85 Complex: a Major Secretion Product of Mycobacterium tuberculosis, Microbiological Reviews, vol. 56, No. 4, p. 648-661, Dec. 1992.
S. D'Souza et al., Mapping of Murine TH1 Helper T-Cell Epitopes of Mycolyl Transferases Ag85A, Ag85B, and Ag85C from Mycobacterium tuberculosis, Infection and Immunity, vol. 71, No. 1, p. 483-493, Jan. 2003.
Jun Wang et al., Single Mucosal, but Not Parenteral, Immunization with Recombinant Adenoviral-Based Vaccine Provides Potent Protection from Pulmonary Tuberculosis, The Journal of Immunology, vol. 173, p. 6357-6365, 2004.
Gopalkrishna Sreejit et al., The ESAT-6 Protein of Mycobacterium tuberculosis Interacts with Beta-2-Microglobulin (β2M) Affecting Antigen Presentation Function of Macrophage, PLOS Pathogens, vol. 10, No. 10, p. 1-19, Oct. 2014.
L Brandt et al., Key epitopes on the ESAT-6 Antigen recognized in mice during the recall of protective immunity to Mycobacterium tuberculosis, The Journal of Immunology, vol. 157 p. 3527-3533, 1996.
Anja Weinreich Olsen et al., Efficient protection against Mycobacterium tuberculosis by vaccination with a single subdominant epitope from the ESAT-6 antigen, Eur. J. Immunol, vol. 30, p. 1724-1732, 2000.
Audrey Tanghe et al., Improved Immunogenicity and Protective Efficacy of a Tuberculosis DNA Vaccine Encoding Ag85 by Protein Boosting, Infection and Immunity, vol. 69, No. 5, p. 3041-3047, May 2001.
T Jefferson et al., Efficacy and effectiveness of influenza vaccines in elderly people: a systematic review, Lancet, vol. 366, p. 1165-1174, Oct. 1, 2005.
Katherine Goodwin et al., Antibody response to influenza vaccination in the elderly: A quantitative review, Vaccine, vol. 24, p. 1159-1169, 2006.
Lone Simonsen et al., Mortality benefits of influenza vaccination in elderly people: an ongoing controversy, Lancet Infect Dis, vol. 7, p. 658-666, Oct. 2007.
Michael L. Jackson et al., Influenza vaccination and risk of community-acquired pneumonia in immunocompetent elderly people: a population-based, nested case-control study, Lancet, vol. 372, p. 398-405, Aug. 2, 2008.
Li Dong et al., An immunostimulatory oligodeoxynucleotide containing a cytidine-guanosine motif protects senescence-accelerated mice from lethal influenza virus by augmenting the T helper type 1 response, Journal of General Virology, vol. 84, p. 1623-1628, 2003.
Sheri M. Eaton et al., Age-related Defects in CD4 T Cell Cognate Helper Function Lead to Reductions in Humoral Responses, The Journal of Experimental Medicine, vol. 200, No. 12, p. 1613-1622, Dec. 20, 2004.
Lixin Zhang et al., An adenoviral vector cancer vaccine that delivers a tumor-associated antigen/CD40-ligand fusion protein to dendritic cells, PNAS, vol. 100, No. 25, p. 15101-15106, Dec. 9, 2003.
Yucheng Tang et al., Multistep process through which adenoviral vector vaccine overcomes anergy to tumor-associated antigens, Blood, vol. 104, p. 2704-2713, Jul. 6, 2004.

(Continued)

Primary Examiner — Robert A Zeman
(74) Attorney, Agent, or Firm — Jacob Frank; Glenn Snyder (57) ABSTRACT A composition/vaccine to intensify and expand the magnitude of the host immune response against the Ag 85 and ESAT6 proteins thereby blocking the inhibitory effect of these two classes of secreted proteins, and thus promoting the clearing or control of the MTb infection. Fusion proteins are created between immunogenic fragments of the soluble secreted MTb proteins Ag 85 and ESAT6 (which are inhibitors of the immune response) and the extracellular domain (ecd) of the immunostimulatory protein ecdCD40 ligand (ecdCD40L). Fusion proteins are created using both Ag85 and ESAT-6 immunogenic peptides and ecdCD40L, to induce a more potent immune response against the MTb than would the use of either protein (Ag85 or ESAT-6) alone. Both a humoral and cellular immune response are induced. The composition/vaccine further avoids the requirement for use of attenuated strains of the tubercle bacillis, to induce an immune response to the Ag85 and ESAT6 proteins.

5 Claims, 2 Drawing Sheets
Specification includes a Sequence Listing.

(56) References Cited

PUBLICATIONS

Hakan Akbulut et al., Antitumor immune response induced by i.t. injection of vector-activated dendritic cells and chemotherapy suppresses metastatic breast cancer, Molecular Cancer Therapeutics, vol. 5, No. 8, p. 1975-1985, Aug. 2006.

Yucheng Tang et al., Vector Prime/Protein Boost Vaccine That Overcomes Defects Acquired during Aging and Cancer, The Journal of Immunology, vol. 177, p. 5697-5707, 2006.

Yucheng Tang et al., Vaccine strategies for cancer and infectious diseases in the elderly, Gene Therapy, p. 2-11, 2007.

Hakan Akbulut et al., Chemotherapy Targeted to Cancer Tissue Potentiates Antigen-specific Immune Response Induced by Vaccine for in Vivo Antigen Loading and Activation of Dendritic Cells, Molecular Therapy, vol. 16, No. 10, p. 1753-1760, Oct. 2008.

Yu Cheng Tang et al., Use of CD40L immunoconjugates to overcome the defective immune response to vaccines for infections and cancer in the aged, Cancer Immunol Immunother, vol. 58, p. 1949-1957, 2009.

TH Han et al., Vector prime protein boost vaccination in the setting of myeloablative-induced lymphopenia suppresses growth of leukemia and solid tumors, Bone Marrow Transplantation, vol. 45, p. 550-557, 2010.

H Akbulut et al., Addition of adenoviral vector targeting of chemotherapy to the MUC-1/ecdCD40L VPPP vector prime protein boost vaccine prolongs survival of mice carrying growing subcutaneous deposits of Lewis lung cancer cells, Gene Therapy, p. 1-8, 2010.

Jeffrey B. Ulmer et al., Expression and immunogenicity of Mycobacterium tuberculosis antigen 85 by DNA vaccination, Vaccine, vol. 15, No. 8, p. 792-794, 1997.

Fernando L. L. Cardoso et al., T-Cell Responses to the Mycobacterium tuberculosis—Specific Antigen ESAT-6 in Brazilian Tuberculosis Patients, Infection and Immunity, vol. 70 No. 12, p. 6707-6714, Dec. 2002.

Anja W. Olsen et al., Protective Effect of a Tuberculosis Subunit Vaccine Based on a Fusion of Antigen 85B and ESAT-6 in the Aerosol Guinea Pig Model, Infection and Immunity, vol. 72, No. 10, p. 6148-6150, Oct. 2004.

* cited by examiner

FIG. 1

FIG. 2

SEQUENCE LISTING

```
<160> NUMBER OF SEQ ID NOS: 7

<210> SEQ ID NO 1
<211> LENGTH: 21
<212> TYPE: PRT
<213> ORGANISM: Artificial Sequence
<220> FEATURE:
<223> OTHER INFORMATION: Synthetic Construct

<400> SEQUENCE: 1

Phe Leu Thr Ser Glu Leu Pro Gly Trp Leu Gln Ala Asn Arg His Val
1               5                   10                  15

Lys Pro Thr Gly Ser
            20

<210> SEQ ID NO 2
<211> LENGTH: 21
<212> TYPE: PRT
<213> ORGANISM: Artificial Sequence
<220> FEATURE:
<223> OTHER INFORMATION: Synthetic Construct

<400> SEQUENCE: 2

Phe Leu Thr Ser Glu Leu Pro Gln Trp Leu Ser Ala Asn Arg Ala Val
1               5                   10                  15

Lys Pro Thr Gly Ser
            20

<210> SEQ ID NO 3
<211> LENGTH: 21
<212> TYPE: PRT
<213> ORGANISM: Artificial Sequence
<220> FEATURE:
<223> OTHER INFORMATION: Synthetic Construct

<400> SEQUENCE: 3

Gly Thr His Ser Trp Glu Tyr Trp Gly Ala Gln Leu Asn Ala Met Lys
1               5                   10                  15

Pro Asp Leu Gln Arg
            20
```

```
<210> SEQ ID NO 4
<211> LENGTH: 20
<212> TYPE: PRT
<213> ORGANISM: Artificial Sequence
<220> FEATURE:
<223> OTHER INFORMATION: Synthetic Construct

<400> SEQUENCE: 4

Gly Thr His Ser Trp Glu Tyr Trp Gly Ala Gln Leu Asn Ala Met Lys
1               5                   10                  15

Gly Leu Gln Ser
            20

<210> SEQ ID NO 5
<211> LENGTH: 16
<212> TYPE: PRT
<213> ORGANISM: Artificial Sequence
<220> FEATURE:
<223> OTHER INFORMATION: Synthetic Construct

<400> SEQUENCE: 5

Gly Gln Ala Met Ala Ser Thr Glu Gly Asn Val Thr Gly Met Phe Ala
1               5                   10                  15

<210> SEQ ID NO 6
<211> LENGTH: 20
<212> TYPE: PRT
<213> ORGANISM: Artificial Sequence
<220> FEATURE:
<223> OTHER INFORMATION: Synthetic Construct

<400> SEQUENCE: 6

Met Thr Glu Gln Gln Trp Asn Phe Ala Gly Ile Glu Ala Ala Ala Ser
1               5                   10                  15

Ala Ile Gln Gly
            20

<210> SEQ ID NO 7
<211> LENGTH: 20
<212> TYPE: PRT
<213> ORGANISM: Artificial Sequence
<220> FEATURE:
<223> OTHER INFORMATION: Synthetic Construct

<400> SEQUENCE: 7

Tyr Gln Gly Val Gln Gln Lys Trp Asp Ala Thr Ala Thr Glu Leu Asn
1               5                   10                  15

Asn Ala Leu Gln
            20
```

COMPOSITION AND METHOD AGAINST TUBERCULOSIS

CROSS-REFERENCE TO RELATED APPLICATIONS

This application claims priority and the benefit under 35 U.S.C. § 119(e) of U.S. Provisional Patent Application No. 62/290,058, filed on Feb. 2, 2016, the disclosure of which is hereby incorporated by reference herein in its entirety.

FIELD OF THE INVENTION

The present invention relates generally to the field of bacterial infections. More specifically, it is directed to novel compositions and methods against the *Mycobacterium Tuberculosis* infection.

BACKGROUND OF THE INVENTION

Background on *Mycobacterium Tuberculosis* (MTb): One third of the earth's population is infected with tuberculosis (1). There were 9.4 million new TB cases worldwide in 2009 (2). Only 10% of these infected individuals develop clinically significant disease. This results in 2 million new deaths per year (1). Twenty percent of individuals exposed to people carrying infectious MTb become infected and 5% of infected develop pulmonary tuberculosis. Five percent of people in the latent state post infection become reactivated (1).

Mechanism Through Which MTb Evades the Human Immune Response and Kills: After phagocytosis by macrophages, MTb can remain alive in the macrophage (1). The surviving tubercle *bacillus* can remain latent in the macrophage for years (1). This is in part due to proteins secreted and released from the tuberculosis bacterial cells, like Ag85A, Ag85B and ESAT-6 (1).

Infected macrophages and dendritic cells displaying peptides from MTb secreted proteins on WIC molecules, can migrate to LN where they induce helper T lymphocyte cell expansion. Expansion of helper T cells contributes to the development of granulomas. While MTb infections are contained and are latent, granuloma are stable but when activated, caseous necrosis occurs (1), following which infectious bacterial cells are released from the granuloma to the neighboring tissue.

MTb has an outer membrane composed of lipids that protect the bacterial cell from drugs and other environmental stresses (3). The chemotherapy of MTb is directed against the enzymes needed for synthesis of the bacterial cell wall (INH and ethambutol). One of these, the Ag85 complex, contains enzymes necessary for the conversion of trehalose monomycolate (TMM) to trehalose dimycolate (TDM) via a transesterification reaction (3).

The Antigen 85 complex: major secretion product of MTb: The family of Ag85 proteins secreted by MTb is the most commonly encountered class of proteins in culture fluid of MTb (4). Ag85A, Ag85B and Ag85C show homology with each other. All 3 are 35 kDa and are fibronectin (FN) binding proteins. All 3 are strongly immunogenic and induce antigen specific antibodies and antigen specific CD8 effector T cells. The Ag85 proteins are associated with the surface of MTb. The Ag85 proteins make up 41% of the tissue culture fluid protein of MTb cultures. Ag85 connects the MTb with FN (4).

Intracellular parasites like MTb escape the immune response by intracellular habitation (4). FN bound to gelatin activates complement receptors, enhancing complement mediated phagocytosis, more strongly than does free FN. Fifty percent of patients develop antibodies to each of the Ag85 proteins: Ag85A, Ag85B and Ag85C (4). Each of these 3 proteins has a very low incidence of positive delayed hypersensitivity tests in guinea pigs infected with MTb. This raises the hypothesis that the release of the Ag85 proteins by MTb protects it from inducing an immune response against the MTb (4).

The amino acid peptide/fragments from AA100 to AA120 of Ag85A and Ag85B are recognized by T cells from the majority of normal human volunteers who are skin test (purified protein derivative) positive (5). This peptide/fragment also is predicted by the EpiMer program to contain human T-cell epitopes from 100-105 (5). In addition, spleen cells from mice vaccinated with plasmids encoding Ag85A and Ag85B react strongly by secreting interferon-gamma when exposed to the AA 100-120 peptide/fragment (5). The AA100-120 peptide/fragment is also cross reactive between Ag85A and Ag85B proteins with respect to induction of immune response in BALB/c mice.

The amino acid sequence (5) of this peptide/fragment (AA 100-AA120) from Ag85A is as follows:

```
                                             SEQ ID NO. 1
          AA-100-FLTSELPGWLQANRHVKPTGS-AA120
```

The amino acid sequence (5) of this peptide/fragment (AA100-AA120) from Ag85B is as follows:

```
                                             SEQ ID NO. 2
          AA-100- FLTSELPQWLSANRAVKPTGS-AA120
```

The amino acid sequence from AA 270-280 is also predicted by the EpiMer program to contain human T-cell epitopes (5). The AA260-280 fragment of Ag85A and Ag85B induce cytokine release from the spleen cells in C57BL/c mice previously vaccinated with plasmid expression vectors encoding Ag85A or Ag85B, and the AA260-280 peptide/fragment of Ag85B induces immune responses in BALB/C mice previously vaccinated with plasmid expression vectors encoding Ag85B (5).

The amino acid sequence (5) of the AA260-280 peptide/fragment of Ag85A is as follows:

```
                                             SEQ ID NO. 3
         AA-260-GTHSWEYWGAQLNAMKPDLQR-AA-280
```

The amino acid sequence (5) of the AA260-280 peptide/fragment of Ag85B is as follows:

```
                                             SEQ ID NO. 4
          AA-260-GTHSWEYWGAQLNAMKGLQS-AA280
```

AdAg85A was administered (6) to BALB/c mice intranasally (IN) in 30 microliters containing $5 \times 10^7$ PFU of replication incompetent AdAg85A or IM, in 50 microliters×2 in hind limb ×2 on the same day.

Then, 4 weeks post vaccination for IM, and 12 weeks post IN vaccination, mice were challenged with live MTb (the H37Rv strain) by inhalation IN or by aerosol: 10,000 CFU of MTb diluted with BS to 24 microliters and delivered into mouse lungs. For aerosol, 100 MTb bacilli were delivered per mouse by inhalation exposure system (6).

There was little protection by week 12 when the vaccine was delivered by IM vaccination but after IN, the level of infectious MTb organisms was reduced in the lungs by 1.3 and 1.5 logs at weeks 4 and 12 post vaccination respectively. The BCG vaccine led to a 1.2 log reduction of infectious MTb organisms in the lung at 4 and 12 weeks, whereas IN administration of an adenoviral vector encoding Ag85A (AdAg85A) led to a 2.3, 2.1 and 1.5 log reduction of infectious MTb organisms in the lungs at 4, 6 and 8 weeks post challenge. Two repeated DNA plasmid Ag85A injections and then respiratory mucosal boosting with AdAg85A gave best the result of all (6).

The ESAT6 Secreted Protein of MTb: The early secreted antigenic target (ESAT-6) is a low molecular weight protein which is secreted by pathogenic MTb. The lymphocytes of a majority of MTb infected patients can recognize ESAT-6. This procedure has been proposed as a test for TB infection (7). The ESAT-6 protein of MTb interacts with beta 2 microglobulin (B2M) interfering with the antigen presentation function of macrophages (7). The carboxylterminal (C-ter) six amino acid residues (90-95) of ESAT-6 were found to be essential for this interaction. The ESAT-6 can enter into endoplasmic reticulum (ER) where it sequesters the B2M (7). This inhibits cell surface expression of MHC1B2M complexes, resulting in down regulation of class I mediated antigen presentation (7). This suggests that ESAT6 undermines the host adaptive immune response.

Crucial host cell functions required for development of anti-MTb immunity like phagosome-lysosome fusion, autophagy, antigen presentation, apoptosis, bactericidal innate immune response are inhibited by pathogenic MTb (7). The proteins secreted by MTb are known to be inhibitory to the immune response against MTb (7). Thus, to inactivate this interference by the C-terminal end of the ESAT6 protein with the host immune response through the binding of B2M, we are proposing to make the 15 AA at the C-ter of ESAT6 (AA 80-95) a target of the proposed composition/vaccine.

The amino acid peptide/fragment sequence (8) of the 15 carboxyl terminal AA of ESAT6 is:

```
                                   SEQ ID NO. 5
AA-80-GQAMASTEGNVTGMFA-AA95
```

ESAT-6 is a major T cell antigen in the low molecular mass antigen fraction of the secreted proteins of MTb (8). ESAT-6 and Ag85B were both recognized by a very high frequency (1:1500 to 1:600) of T cells during the recall of immunity (8). Mice immunized with intact ESAT-6 protein mixed with adjuvant showed induction of both cellular and humoral immune response (29).

To localize epitopes on ESAT-6 which are recognized by T cells, a series of 9 synthetic 20-AA peptides was synthesized based on previously published sequence of ESAT-6 protein (8). Splenic lymphocytes were stimulated with this panel of peptides from the amino terminus (N-ter) of ESAT-6 14 days after vaccination. Mice were then killed and cells from draining lymph nodes were stimulated in vitro with short term culture filtrate and the production of IFN-gamma in vitro was measured (8). Sites recognized by T cells were monitored by release of INF-gamma.

Two peptides were identified as positive: P1 (AA1-20) and P6 (AA51-70). The AA sequences (8) of these two peptides/fragments are as follows:

```
                                   SEQ ID NO. 6
P1 (AA1-20): MTEQQWNFAGIEAAASAIQG
```

-continued

```
                                   SEQ ID NO. 7
P6 (AA51-70): YQGVQQKWDATATELNNALQ
```

The P6 was highly stimulatory for the A/J, CBA/J, and AKR/N strains of mice, whereas the C57BL/6J and BALB/c mouse strains recognized an epitope at the N-ter in the first 20 AA (8).

Free peptides were emulsified with dimethyl dioctadecylammonium bromide/monophosphoryl Lipid and tested by IV administration and by aerosol administration in a model of MTb in mice (9). Groups of B6CBAF1 hybrid mice were vaccinated with ESAT-6P1 or ESAT-6P6 (10 micrograms) 3×, each vaccination separated by 3 weeks. The vaccines were administered IV or by aerosol. Lymphocyte responses were evaluated 3 weeks after the last vaccination (21). Intact ESAT-6 and the ESAT-6 peptides were used to stimulate the lymphocytes and then IFN-gamma release was measured.

Although both peptides induced a cellular Th1 immune response, only the 51-70 epitope protected challenged mice (the F1 hybrid strain of B6CGAF1 mice) and the level of protection was equivalent to that achieved with intact ESAT-6 and BCG (9).

The survival of ESAT-6 peptide immunized mice was compared with the survival of mice that were immunized with the filtrate of the supernatant or medium in which were grown short term culture of cells infected with MTb (9). The survival of mice that were vaccinated by BCG was used as a positive control. Two weeks after vaccination was completed, the mice were challenged by MTb administered by aerosol or IV ($5\times10^4$ CFU MTb 10 weeks after the primary vaccination). MTb bacterial titers were measured in organs (lung and spleen) 10 weeks (aerosol) or 2 weeks (IV) following challenge (21). BCG, the ultrafiltrate of infected cells and the P6 but not the P1 peptide reduced the level of live MTb bacterial cells in the mice by 1 log (9).

Compositions/Vaccines for Tuberculosis

BCG is an attenuated mycobacterial *bovis* strain which has been in use as a vaccine since 1920 (1). It has been long observed that the bacterial strain vaccine is effective in children as a live vaccine but is not effective when delivered as an inactivated killed vaccine. This is presumably due to the fact that the live tubercle bacilli secrete several immunogenic proteins (Ag85 and ESAT6) which become targets of the immune response. Interestingly, these two classes of proteins each inactivate the host immune response against the tubercle *bacillus*.

One goal of vaccination is the induction of release of interferon gamma, IL2, and TNF alpha from immunoreactive cells leading to expansion of antigen specific memory CD4 T cells, CD 8 T cell expansion, and presentation of Class I MEW antigens to induce expansion of CD8 effector T cells. Another goal is the inactivation of the function of the soluble proteins released by the tubercle bacillis, which interfere with the development of the host immune response to the MTb bacterial infection.

Vaccine strategies against the Ag85 family of proteins have involved administration of the Ag85 proteins, the proteins emulsified with adjuvant, DNA plasmid expression vectors encoding the Ag85 proteins, and adenoviral and other viral expression vectors encoding the Ag85 proteins (10).

Shortcomings of Current Vaccine Strategies: The MTb BCG vaccine, which is a bovine live but attenuated bovine tuberculosis bacterial cell vaccine, is good as a protection from infection for children but protection is lost after 10-15 years (1). The requirement for use of attenuated strains of the tubercle bacillis, in order to induce an immune response to the Ag85 and ESAT6 proteins, is a limitation which is circumvented by the proposed vaccine invention described in this application.

SUMMARY OF THE INVENTION

Figure 1:
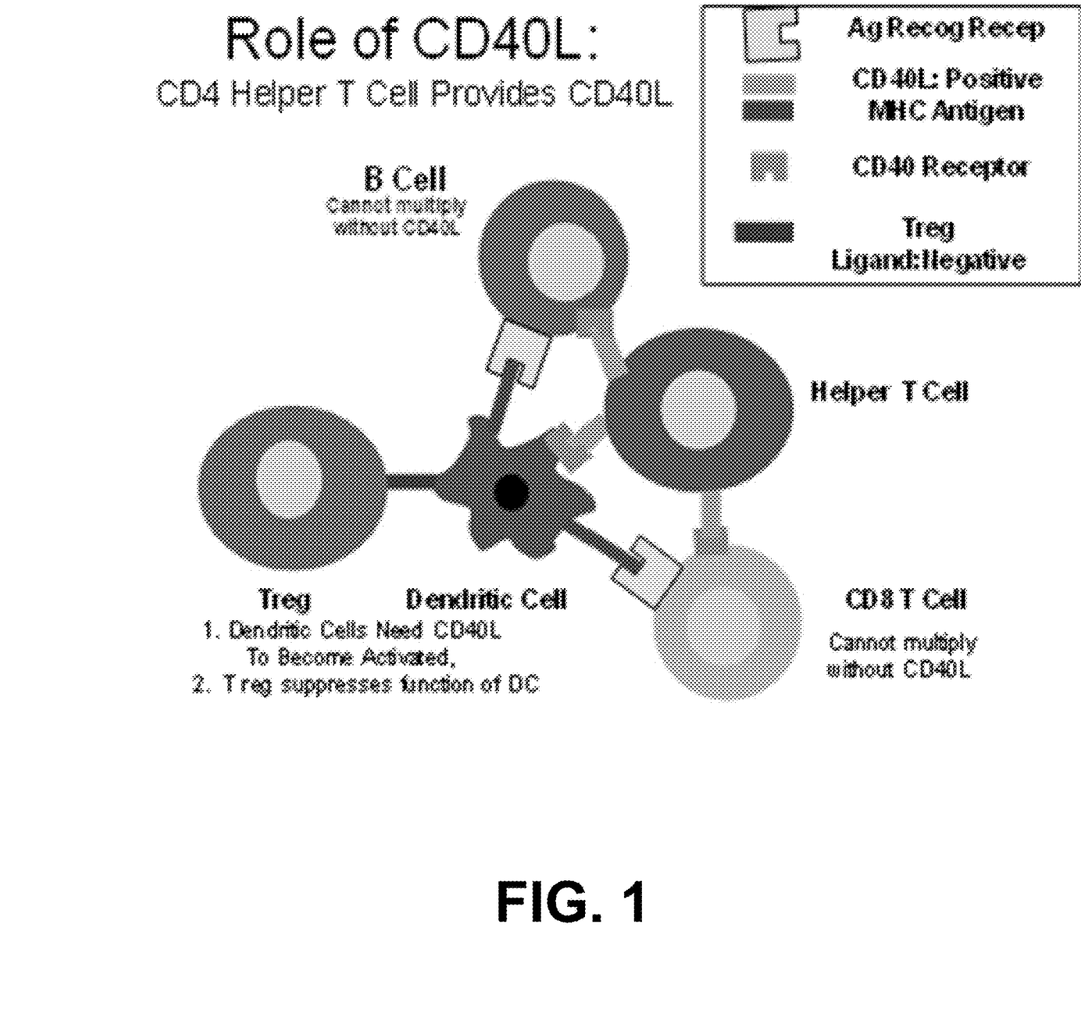
Figure 2:
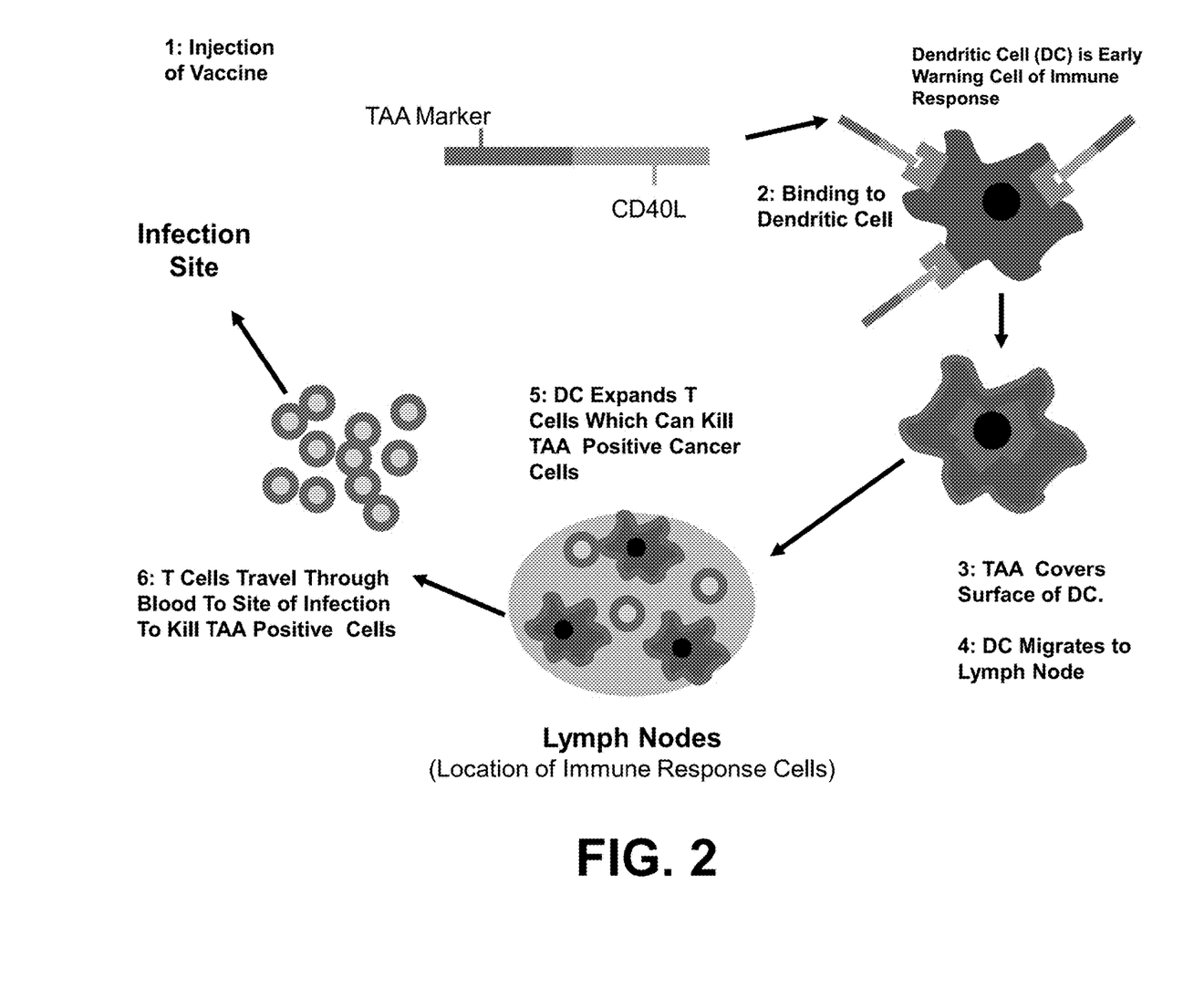

Applicant's invention provides for a composition/vaccine to overcome deficiencies of the prior art by creation of fusion proteins between immunogenic fragments of the soluble secreted MTb proteins Ag 85 and ESAT6 (which are inhibitors of the immune response) and the extracellular domain (ecd) of the immunostimulatory protein ecdCD40 ligand (ecdCD40L). Fusion proteins are created using both Ag85 and ESAT-6 immunogenic peptides and ecdCD40L, to generate a more potent immune response against the MTb than would the use of either protein (Ag85 or ESAT-6) alone. Both a humoral as well as a cellular immune response are generated.

The composition/vaccine intensifies and expands the magnitude of the host immune response against the Ag 85 and ESAT6 proteins thereby blocking the inhibitory effect of these two classes of secreted proteins, and thus promoting the clearing or control of the MTb infection. Applicant's composition/vaccine further avoids the requirement for use of attenuated strains of the tubercle bacillis, to induce an immune response to the Ag85 and ESAT6 proteins.

The composition/vaccine simultaneously uses the two major proteins secreted by MTb as each of these two proteins block the generation of an adaptive immune response against MTb, whereby induction of a neutralizing antibody immune response against these two proteins will reduce their ability to block the immune response to MTb, thereby using the inactivation of the immunoinhibitory MTb proteins as a way to overcome the current limitations of the BCG vaccines (limited duration of protective effect and inability to clear the infection).

The composition/vaccine may be administered as a mixture of plasmid DNA expression vectors which encode fusion proteins comprised of immunogenic fragment(s) of the Ag85A and Ag85B proteins with the ESAT6 protein. The composition/vaccine provides for a composition/vaccine having both long term shelf life, as well as long term protection for individuals of all ages.

BRIEF DESCRIPTION OF THE DRAWINGS

FIG. 1 illustrates an overview of the application of the TAA/ecdCD40L vaccine platform in an individual's immune system, in which a fragment of the target associated antigen (TAA) is attached to the extracellular domain (ecd) of the potent immune-stimulatory protein CD40L.

FIG. 2 further illustrates the binding of the TAA/ecdCD40L protein to the CD40 receptor on dendritic cells (DCs) as well as on B cells and T cells, activates these cells by replacing the CD40L and once engaged on the CD40 receptor, the TAA/ecdCD40L protein is internalized into the DC that allows the TAA to be processed through the Class I and Class II MHC presentation pathways.

DETAILED DESCRIPTION OF THE INVENTION

Background of the Invention—The TAA/ecdCD40L Composition/Vaccine Platform: Another factor besides lack of potency and a limited memory response that could prevent the success of any composition/vaccine including a tuberculosis composition/vaccine is that individuals being vaccinated who are of advanced chronological age (11-14), debilitated, or immunosuppressed by the presence of chronic disease or a pre-existing infection with human immunodeficiency virus (HIV) (1), do not respond well to vaccination due to the diminished expression of CD40L in the CD40L helper T cells of these people (15-16). The presence of the CD40L on CD4 helper T cells is necessary for the expansion of antigen specific T cells and B cells as a result of vaccination.

In order to overcome these problems, the Applicant's laboratory (17-25) developed a TAA/ecdCD40L (TAA-target associated antigen) composition/vaccine platform that is specifically designed to overcome the defective response to vaccination in immunosuppressed, debilitated patients who are of advanced chronological age. The basis for the success of this vaccine is that it supplies a potent immunostimulatory signal (ecdCD40L) that is missing in older people and thought to be one of the reasons for the diminished response of older individuals to vaccination (15-16). This vaccination is customarily given subcutaneously (SC) either as a TAA/ecdCD40L protein, or as an Ad-sig-TAA/ecdCD40L vector prime-TAA/ecdCD40L protein boost (17-25).

Background on Poor Response to Vaccine Among Individuals of Advanced Chronological Age, or Who are Chronically Infected, or Otherwise Debilitated: The response to vaccination may be limited by several factors: low immunogenicity of the target antigen, the state of health and the age of the individual, and pre-existing conditions in the subject to be vaccinated such as chronic infections or cancer, or other host factors which lead to defective function of CD8 T cells, CD4 T cells, B cells, and dendritic cells. Many of these involve defective expression of the CD40L on CD4 helper T cells. As shown in FIG. 1, such diminished expression of CD40L on CD 4 helper T cells can lead to a diminished response to vaccination. This is due to the fact the engagement of the CD40 receptor on antigen specific B and CD8 T cells by the CD40L on the surface of CD4 helper T cells is an essential step for these cells to expand in number in response to vaccination (see FIG. 1).

The Applicant's laboratory (17-25) has found that the linkage of the target antigen or a piece of the target antigen to the extracellular domain (ecd) of the CD40L results in a dramatic increase in the magnitude of the immune response induced by vaccination in young as well as older test subjects. This composition/vaccine strategy converts weak antigens into potent immunogens, and overcomes states of anergy due to central or peripheral tolerance.

The loss of expression of CD40L in the activated CD4 helper T cells of older individuals, reduces the ability of the adaptive immune response to respond to vaccination (15-16). This is an example of the importance of the presence of the CD40L in the immune response (see FIG. 1). In older individuals, the absence of the presentation of the CD40L on activated CD4 helper T cells, reduces the magnitude of the immune response to influenza vaccination. Recent analyses of human influenza vaccination clinical data show that less than 20% of individuals above 55 years of age develop a fully protective neutralizing antibody response to the yearly multivalent particle inactivated human influenza vaccine (11-14). This is due to the acquisition of both quantitative as well as qualitative defects such as loss of expression of CD40 ligand (CD40L) on CD4 helper T cells during activation (15-16) in the immune response as individuals reach the $5^{th}$ and $6^{th}$ decades of life.

TAA/ecdCD40L Vaccine Platform: In order to generate a composition/vaccine that can dramatically increase the potency of the immune response in healthy subjects, as well as subjects in whom the function of CD4 helper T cells is defective and thereby circumvent the functional defects in the immune response that are acquired in such individuals, as well as increase the immunogenicity of weak antigens, such as those present in MTb, the Applicant's laboratory (17-25) designed the TAA/ecdCD40L vaccine strategy. Two versions of this composition/vaccine are as follows: 1. one in which the TAA/ecdCD40L transcription unit is embedded in a replication incompetent adenoviral vector (Ad-sig-TAA/ecdCD40L) which is used as an initial priming injection, followed by two sc injections of the TAA/ecdCD40L protein, and 2. a second one in which the vaccine consists solely of the TAA/ecdCD40L fusion protein. The TAA is connected through a linker to the amino-terminus of the extracellular domain (ecd) of the potent immunostimulatory signal CD40 ligand (CD40L). The attachment of the TAA to the CD40L accomplishes two things: 1. as shown in FIG. 2, the binding of the TAA/ecdCD40L protein to the CD40 receptor on the dendritic cells (DCs) as well as on the B cells and T cells, activates these cells by replacing the CD40L signal which is missing on the plasma membrane of the CD4 helper T cells of older individuals (12-13); 2. once the TAA/ecdCD40L protein is engaged on the CD40 receptor of the DC, the entire TAA/ecdCD40L protein is internalized into the DC in a way that allows the TAA to be processed through the Class I as well as the Class II WIC presentation pathways (17-25).

The activated TAA loaded dendritic cells (DC) then migrate to the regional lymph nodes (15) where they can activate and induce expansion of the TAA specific CD8 effector T cells. These antigen specific CD8 effector cells become increased in number in the lymph nodes (17-18, 20), following which they egress from the lymph nodes into the peripheral blood. The antigen specific CD8 effector T cells then exit the intravascular compartment and enter into the extravascular sites of inflammation or infection (16). In addition to showing that this vaccine increases the antigen specific CD8 effector T cells in the sites of inflammation, we have shown that the activation and expansion of the B cells by the TAA/ecdCD40L protein increases the levels of the TAA specific antibodies in the serum (17-25).

In this specification, although the preferred embodiments have been described in detail, it should be understood that various changes, substitutions and alterations may be made therein without departing from the spirit and scope of the invention. Therefore, the specification is to be regarded in an illustrative rather than a restrictive sense.

The use of the terms "a" and "an" and "the" and similar referents in the context of describing the invention, are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in a suitable order unless otherwise indicated herein or otherwise clearly contradicted by context.

As used herein, the term "antigen" refers broadly to any antigen or portion thereof to which a human, mammal, bird or other animal can generate an immune response. "Antigen" as used herein refers broadly to a molecule that contains at least one antigenic determinant to which the immune response may be directed. The immune response may be cell-mediated, humoral or both.

As used herein, "antigenic determinant" refers to a single antigenic site or epitope on a complex antigenic molecule or particle, a minimal portion of a molecule that interacts with an antibody or T cell receptor. Antigenic determinants may be linear or discontinuous.

"Pharmaceutically acceptable" in the context of the present invention means a pharmaceutical composition that is generally safe, non-toxic and biologically acceptable for veterinary and human pharmaceutical use. Preferred compositions of this invention are intended for humans or animals.

The phrase "an effective amount" in reference to administering the fusion protein or an expression vector encoding that protein, is an amount that results in an increase in the immune response as measured by an increase in T cell activity and/or antibody production.

The fusion protein recited herein may be formulated with an adjuvant to enhance the resulting immune response. As used herein, the term "adjuvant" in the context of the instant invention means a chemical that, when administered with the expression vector or the fusion protein, enhances the immune response. An adjuvant is distinguished from a carrier protein in that the adjuvant is not chemically coupled to the antigen. Adjuvants are well known in the art and include, but not limited to, mineral oil emulsions (U.S. Pat. No. 4,608,251) such as Freund's complete or Freund's incomplete adjuvant (Freund, *Adv. Tuberc. Res.* 7:130 (1956); Calbiochem, San Diego Calif.), aluminum salts, especially aluminum hydroxide or ALHYDROGEL (approved for use in humans by the U.S. Food and Drug Administration), muramyl dipeptide (MDP) and its analogs such as [Thr$^1$]-MDP (Byersand Allison, *Vaccine* 5:223 (1987)), monophosphoryl lipid A (Johnson et al., *Rev. Infect. Dis.* 9:S512 (198)), and the like.

The term "vector" which contains a transcription unit (aka the "expression vector") as used herein refers to viral and non-viral expression vectors that when administered in vivo can enter target cells and express an encoded protein. Viral vectors suitable for delivery in vivo and expression of an exogenous protein are well known and include adenoviral vectors, adeno-associated viral vectors, retroviral vectors, vaccinia vectors, pox vectors, herpes simplex viral vectors, and the like. Viral vectors are preferably made replication defective in normal cells. For example, see U.S. Pat. Nos. 6,669,942; 6,566,128; 6,794,188; 6,110, 744; 6,133,029. The vector can be administered parenterally, such as intravascularly, intravenously, intra-arterially, intramuscularly, subcutaneously, or the like. Administration can also be orally, nasally, rectally, transdermally or aerosol inhalation. The vectors may be administered as a bolus, or slowly infused. The vector in the instant application is preferably administered subcutaneously.

The term "transcription unit" as it is used herein in connection with an expression vector means a stretch of DNA that is transcribed as a single, continuous mRNA strand by RNA polymerase, and includes the signals for initiation and termination of transcription. For example, in one embodiment, a transcription unit of the invention includes nucleic acid that encodes from 5' to 3' a secretory signal sequence, an influenza antigen and CD40 ligand. The transcription unit is in operable linkage with transcriptional and/or translational expression control elements such as a promoter and optionally any upstream or downstream enhancer element(s). A useful promoter/enhancer is the cytomegalovirus (CMV) immediate-early promoter/enhancer. See U.S. Pat. Nos. 5,849,522 and 6,218,140.

The term "CD40 ligand" (CD40L) as used herein refers to a full length or portion of the molecule known also as CD154 or TNF5. CD40L is a type II membrane polypeptide having a cytoplasmic domain at its N-terminus, a transmembrane region and then an extracellular domain ("ecd") at its C-terminus. Unless otherwise indicated the full length CD40L is designated herein as "CD40L," "wtCD40L" or "wtTmCD40L." The nucleotide and amino acid sequence of CD40L from mouse and human is well known in the art and can be found, for example, in U.S. Pat. No. 5,962,406. Also, included within the meaning of CD40 ligand are variations in the sequence including, but not limited to, conservative amino acid changes and the like which do not alter the ability of the ligand to elicit an immune response in conjunction with the fusion protein of the invention. The CD40L is a biological trimer, and each of the fragments in a fusion protein is limited in amino acid size so as not to destabilize the CD40L trimer.

The term "neutralizing antibody" as used herein refers to antibodies that reduce the virulence, infectivity or pathogenicity of *C difficile* by partial or complete inactivation of one or more *C difficile* virulence factors.

The term "opsonizing antibody" as used herein refers to antibodies that bind to a receptor on *C difficile* and "mark" it for subsequent ingestion and destruction by phagocytes such as macrophages. In this context, an opsonizing antibody attaches to one or more *C difficile* virulence factors and acts as a binding enhancer for phagocytosis by macrophages The term "secretion" in reference to the fusion protein TAA/ecdCD40L, means that the fusion protein includes elements (such as the secretory or signal sequence) that cause secretion of the TAA/ecdCD40L fusion protein to occur, as opposed to an element such as a transmembrane domain of a cell that does not allow secretion to occur.

Some of the abbreviations used herein include: "Ad" (adenoviral); "sig" (signal sequence); "TAA" (target associated antigen); "ET" (epitope target); "ecd" (extracellular domain); and "sc" (subcutaneous).

The term "secretory signal sequence" (aka. "signal sequence," "signal peptide," leader sequence," or leader peptide") as used herein refers to a short peptide sequence, generally hydrophobic in charter, including about 20 to 30 amino acids which is synthesized at the N-terminus of a polypeptide and directs the polypeptide to the endoplasmic reticulum. The secretory signal sequence is generally cleaved upon translocation of the polypeptide into the endoplasmic reticulum. Eukaryotic secretory signal sequences are preferred for directing secretion of the exogenous gene product of the expression vector. A variety of suitable such sequences are well known in the art and include the secretory signal sequence of human growth hormone, immunoglobulin kappa chain, and the like. In some embodiments, the endogenous tumor antigen signal sequence also may be used to direct secretion.

The term "linker" as used employed in this application with respect to the transcription unit of the expression vector refers to one or more amino acid residues between the carboxy terminal end of the antigen and the amino terminal end of CD40 ligand. The composition and length of the linker may be determined in accordance with methods well known in the art and may be tested for efficacy. (See, e.g. Arai et al. Protein Engineering, Vol. 4, No. 8, 529-532, August 2001). In certain embodiments of the present invention, the linker is generally from about 3 to about 15 amino acids long, more preferably about 5 to about 10 amino acids long. However, longer or shorter linkers may be used or the linker may be dispensed with entirely. Longer linkers may be up to about 50 amino acids, or up to about 100 amino acids. One example of a linker well-known in the art is a 15 amino acid linker consisting of three repeats of four glycines and a serine (i.e., [Gly$_4$Ser$_3$).

Description of Operation of the Ag85/ecdCD40L and the ESAT6/ecdCD40L Compositions/Vaccines: MTb secretes the Ag85 and ESAT6 proteins, each of which inactivates the host immune response against the MTb infection. At the same time these two protein classes are inactivating the immune response against MTb, they are inducing an immune response against themselves because they are immunogenic proteins. The invention is based on the creation of fusion proteins between immunogenic fragments of these soluble secreted MTb proteins (which are inhibitors of the immune response) and the extracellular domain (ecd) of the immunostimulatory protein ecdCD40 ligand (ecdCD40L). The goal is to intensify and expand the magnitude of the host immune response against the Ag 85 and ESAT6 proteins, thereby blocking the inhibitory effect of these two classes of secreted proteins, and thus promoting the clearing or control of the MTb infection.

Method of Construction of the Ag85/ecdCD40L and the ESAT6/ecd/CD40L Vaccines: A cDNA for each of the Ag85 or ESAT6 peptides will be attached via a cDNA encoding an 8 amino acid linker to the N-ter of the extracellular domain (ecd) of the CD40L. Each of these cDNAs, encoding one of the above described secretable MTb/ecdCD40L proteins, will be inserted into a plasmid DNA expression vector system encoding a MTb/ecdCD40L fusion protein (26) and administered intramuscularly (IM) or intranasally (IN). 10 micrograms of plasmid expression vector encoding fusion proteins comprised of immunogenic fragments of the Ag85 or ESAT6 proteins attached to the ecdCD40L will be injected IM 3× at 3 week intervals. Such a dose and schedule resulted in induction of Ag85 specific cytotoxic lymphocytes and antibodies (26) in previous vaccinations with Ag85. Injection of mice with DNA encoding the secreted Ag85 protein conferred protection against challenge with *Mycobacterium bovis* (26).

The ability to protect mice from lethal challenges of MTb may be tested at varying doses of tubercle *bacillus* in permissive mouse strains (BALB/c or C57BL/J) by vaccination (IM injection or IN application every 3 weeks for 3 successive injections) of a mixture of the following seven pMTb/ecdCD40L plasmids as follows:

a. pAg85A$_{100-120}$/ecdCD40L
    b. pAg85A$_{260-280}$/ecdCD40L
    c. pAg85B$_{100-120}$/ecdCD40L
    d. pAg85B$_{260-280}$/ecdCD40L
    e. pESAT6P1$_{1-20}$/ecdCD40L
    f. pESAT6P6$_{51-70}$/ecdCD40L
    g. pESAT6$_{80-95}$/ecdCD40L The Ag85A, Ag85B and ESAT6 proteins are all secreted by MTb. These are not transmembrane proteins that are stabilized in the membrane. These proteins are secreted so that they are outside of the MTb cell. Therefore, they are available for the immune response just like peptides in the extracellular domain of transmembrane proteins.

Mixtures of the compositions/vaccines for Ag85 and ESAT6 have been shown to be superior to either of the compositions/vaccines administered alone: T cell responses to MTb are primarily directed to specific antigens on the secreted proteins Ag85 or ESAT-6 (27). Ag85B induces strong T cell proliferation and IFN-gamma secretion (27).

ESAT-6 (early secreted antigenic target) is a low molecular weight protein in pathogenic MTb (27). Ag85B DNA vaccine (27) and ESAT-6 (27) were able to induce protection in a murine model of TB. Co-immunization with these two proteins resulted in greater protection (27) than achievable when either protein was used alone as a composition/vaccine. Therefore, the proposed vaccine strategy will be administered as a mixture of plasmid DNA expression vectors which encode fusion proteins comprised of immunogenic fragments of the Ag85A and Ag85B proteins with the ESAT6 protein.

A fusion protein comprised of fragments of Ag85 with ESAT-6 prolonged survival post challenge whereas the individual proteins did not (28). Compositions/Vaccines given 3×SC with 3 week intervals. Skin tests were carried out at 4 weeks after vaccination using DTH reactions (28). Guinea pigs were challenged 12 weeks after the initial vaccination (6 weeks after the third vaccination). Control animals mean survival time (MST) 83 days (28). ESAT-6 vaccinated mice had a MST of 129 days. The Ag85B vaccinated had MST of 143 days. The MST of BCG and fusion protein not reached at 200 days (28).

Advantages of the Ag85/ecdCD40L and ESAT6/ecdCD40L Compositions/Vaccines for Tuberculosis: MTb secretes the Ag85 and ESAT6 proteins, each of which inactivates the host immune response against the MTb infection. At the same time that these two protein classes are inactivating the immune response against MTb, they are inducing an immune response against themselves because they are immunogenic proteins. The invention is based on the creation of fusion proteins between immunogenic fragments of these soluble secreted MTb proteins (which are inhibitors of the immune response) and the extracellular domain (ecd) of the immunostimulatory protein ecdCD40 ligand (ecdCD40L). The goal is to intensify and expand the magnitude of the host immune response against the Ag85 and ESAT6 proteins, thereby blocking the inhibitory effect of these two classes of secreted proteins, and thus promoting the clearing or control of the MTb infection.

The following is a list of unique features and advantages of the inventive composition/vaccine:
1. This composition/vaccine will provide an immunization procedure that in contradistinction to the available vaccine for tuberculosis in the USA will overcome the obstacles that pre-existing conditions (chronic disease, HIV, advanced chronological age) now pose for the existing compositions/vaccines (BCG).
2. The current composition/vaccine for MTb (BCG) has limited memory and it is proposed that the use of the MTb/ecdCD40L fusion proteins will enhance the memory response for a time period that is longer than the current BCG vaccine.
3. The selection of the target for the MTb/ecdCD40L as the two major proteins secreted by MTb is another unique feature of the inventive composition/vaccine. Each of these two proteins block the generation of an adaptive immune response against MTb. The induction of a neutralizing antibody immune response against these two proteins will reduce their ability to block the immune response to MTb. As an example, the fragment of ESAT-6 (AA90-95) is known to be necessary for the binding of the ESAT-6 protein to the Bbeta-2-microglobulin protein. Induction of antibodies which bind this fragment of ESAT-6 will reduce the inhibition of the host immune response that is induced by the binding of the ESAT-6 protein to beta-2-mciroglobulin. This is the first time that a MTb composition/vaccine strategy has been proposed that relies on the inactivation of the immunoinhibitory MTb proteins as a way to overcome the current limitations of the BCG vaccines (limited duration of protective effect and inability to clear the infection). All previous vaccines fail to clear the infected individual of infectious MTb bacterial cells. The creation of fusion proteins between the Ag85 and ESAT-6 immunogenic peptides and ecdCD40L will generate a more potent immune response against the MTb than would the use of either protein alone.
4. The use of fusion protein compositions/vaccines comprised of peptides from AG85 and ESAT-6 to the ecdCD40L will also induce a MTb specific cellular immune response against the MTb infected cells which will lead to clearance of all MTb infectious organisms (which the existing BCG vaccine cannot accomplish).
5. The proposed composition/vaccine will be able to clear the infection by virtue of the neutralizing antibodies that disable the function of the Ag85 and ESAT-6 proteins which is to block the development of presentation of MTb proteins on Class I and Class II WIC.
6. The inventive composition/vaccine is a recombinant composition/vaccine which does not require use of live attenuated MTb bacterial cells in order to induce an immune response to the secreted proteins Ag85 and ESAT6 which interfere with the immune response of the infected individual against MTb. Finally, by inducing an antibody response to the AG85A, AG85B and ESAT6 proteins, the antibodies induced may prevent the interference that these secreted MTb proteins cause in the evolution of an immune response by the infected individual against the MTb.
7. The induction of release of interferon gamma, IL2, and TNF alpha from immunoreactive cells leading to expansion of antigen specific memory CD4 T cells, CD 8 T cell expansion, and presentation of Class I WIC antigens, to induce expansion of CD8 effector T cells.

REFERENCES

1. Skeiky and Sadoff. Nature Reviews Microbiology 4: 469-476, 2006.
2. Critical Reviews in Microbiology 40: 117-145, 2014.
3. Expert Reviews Anti Infective Therapy 10: 1023-1036, 2012.
4. Microbiological Reviews 56: 648-661, 1992.
5. Infection and Immunity 71: 483-493, 2003.
6. J. Immunology 173: 6357-6365 2004.
7. PLoS Pathogens October, 2014 Volume 10: e1004446.
8. J. Immunology 157: 3527-3533, 1996.
9. European J Immunology 30: 1724-1732, 2000.
10. Infection and Immunity 69: 3041-3047, 2001.
11. Jefferson T, Rivetti D, Rivetti A, Rdin M, Di Pietrantonj C, and Demicheli V. Efficacy and effectiveness of influenza vaccines in elderly people: a systematic review. Lancet 366, 1165-1174, 2005.
12. Goodwin K, Viboud C, and Simonsen L. Antibody response to influenza vaccination in the elderly: a quantitative review. Vaccine 24, 1159-1169, 2006.
13. Simonsen L et al., Lancet Inf. Dis 7: 658-666, 2007.
14. Jackson M L et al., Lancet 372: 398-405, 2008.
15. Dong L, More I, Hossain J M, Liu B, and Kimjra Y. An immunostimulatory oligodeoxynucleotide containing a cytosine-guanosine motif protects senescence-accelerated mice from lethal influenza virus by augmenting the T helper type 1 response. Journal of General Virology 84, 1623-1628, 2003.
16. Eaton S M et al J. Exp. Med. 200: 1613-1622, 2004.

17. Zhang L, Tang Y, and Deisseroth A: Adenoviral vectors encoding a secretable HPV 16 E7/CD40 ligand fusion protein induce immunity for up to one year in a murine model. *PNAS,* 100: 15101-15106, 2003.
18. Tang, Y, Zhang, L, Yuan, J, Maynard, J, and Deisseroth, A. Multi-step process of vector mediated activation and tumor antigen loading of APC by CD40 ligand/tumor antigen secretory protein generates protection from cancer cell lines. *Blood,* 104: 2704-2713, 2004.
19. Akubulut H, Tang Y C, Maynard J, and Deisseroth A. Dendritic cells improve the efficacy of vector targeted chemotherapy in breast cancer. *Molecular Cancer Therapeutics* 5: 1975-1985, 2006.
20. Tang, Y C, Maynard J, Akbulut H, Fang X M, Zhang W W, Xia X Q, Koziol J, Linton P J, and Deisseroth. Vector Prime/Protein Boost Vaccine Which Overcomes Defects Acquired During Aging and Cancer. *J. Immunology,* 177: 5697-5707, 2006.
21. Tang Y, Akbulut H, Maynard J, Zhang L, Petersen L, and Deisseroth A. Vaccine strategies for cancer and infectious diseases in the elderly. Gene Therapy 2007, Edited by T. Ochiai, H. Shimada, and M. Tagawa, Chiba, Japan, pp. 78-85, 2007.
22. Akbulut H, Tang Y C, Maynard J, and Deisseroth A. Chemotherapy targeted to cancer tissue potentiates antigen specific immune response induced by vaccine for antigen loading and activation of dendritic cells. Molecular Therapy, 10: 1753-1760, 2008.
23. Tang, Y C, Linton, P J, Thoman M, and Deisseroth A. Symposium in Writing: Vaccine for Infections and Cancer. Cancer Immunology Immunotherapy 58: 1949-1957, 2009.
24. Han T H, Park Y H, Maynard J, Li P C, Tang Y C, and Deisseroth A. Ad-sig-BcrAbl/ecdCD40L Vector Prime-BcrAbl/ecdCD40L Protein BoostVaccine for P210Bcr-Abl Protein, Bone Marrow Transplantation, 45: 550-557, 2010.
25. Akbulut H, Tang Y C, Akbulut G, Maynard J, and Deisseroth A. Vaccine combined with vector targeted chemotherapy reduces levels of cancer stem cells and improves outcome of cancer treatment, Gene Therapy 17: 1333-1340, 2010.
26. Vaccine 15: 792-794, 1997.
27. Infection and Immunity 70: 6707-6714, 2002.
28. Infection and Immunity 72: 6148-6150, 2004.

The invention claimed is:

1. A composition comprising three expression vectors, each expression vector comprising a transcription unit encoding one of three different human secretable TAA/ecdCD40L (target associated antigen/extracellular domain CD40 ligand) fusion proteins comprising:
  (i) a first fusion protein in which the TAA targeted fragments comprising the sequence of SEQ ID NO. 1 and SEQ ID NO. 2 respectively from proteins Ag85A and Ag85B, a second fusion protein in which the TAA targeted fragments comprise the sequence of SEQ ID NO. 3 and SEQ ID NO. 4 respectively from proteins Ag85A and Ag85B, and a third fusion protein in which the TAA targeted fragments comprise the sequence of SEQ ID NO. 5, SEQ ID NO. 6, and SEQ ID NO. 7 from protein ESAT6, where each of said TAA targeted fragments is distinct from one another, (ii) a secretory signal sequence for directing secretion for each of the fusion proteins, and (iii) wherein each of said three TAA targeted fragments is linked to the amino terminal end of an ecdCD40L to respectively define the first, second and third fusion proteins corresponding to a first, second and third one of said three expression vectors, wherein said three expression vectors collectively define a multi-fragment TAA/ecdCD40L fusion protein composition.

2. The composition of claim 1, wherein each of said fusion proteins further comprises one or more adjuvants and a pharmaceutically acceptable carrier.

3. The composition of claim 1, wherein said expression vectors are adenoviral expression vectors.

4. The composition of claim 1, wherein the expression vectors are plasmids.

5. A method of inducing an immune response against MTb in an individual comprising administering to said individual an effective amount of the composition of claim 1 as a single dose or as multiple doses.

* * * * *